United States Patent [19]

Gyory et al.

[11] Patent Number: 5,240,995
[45] Date of Patent: * Aug. 31, 1993

[54] ELECTROTRANSPORT ADHESIVE

[75] Inventors: J. Richard Gyory, Los Altos; Ronald P. Haak, Cupertino; Felix Theeuwes, Los Altos; Patrick J. Lew, Mountain View, all of Calif.

[73] Assignee: ALZA Corporation, Palo Alto, Calif.

[*] Notice: The portion of the term of this patent subsequent to Aug. 10, 2010 has been disclaimed.

[21] Appl. No.: 741,475

[22] PCT Filed: Feb. 8, 1990

[86] PCT No.: PCT/US90/00727

§ 371 Date: Aug. 6, 1991

§ 102(e) Date: Aug. 6, 1991

Related U.S. Application Data

[63] Continuation of Ser. No. 308,716, Feb. 9, 1989.

[51] Int. Cl.⁵ .............................................. C08G 63/48
[52] U.S. Cl. .................................. 525/57; 525/58; 525/59; 525/61; 525/931; 525/937; 525/941; 524/52; 524/54; 524/57; 524/925; 604/20; 607/149
[58] Field of Search ............... 604/20; 128/802; 525/57, 58, 59, 61, 931, 937, 941; 524/52, 54, 57, 925

[56] References Cited

U.S. PATENT DOCUMENTS

| | | | |
|---|---|---|---|
| 2,624,890 | 6/1953 | Leader | 167/58 |
| 2,997,399 | 8/1961 | Eberhard et al. | 106/35 |
| 3,475,363 | 10/1969 | Gander | 260/29.7 |
| 3,564,078 | 2/1971 | Wicker et al. | 260/881 |
| 3,574,153 | 4/1971 | Sirota | 260/8 |
| 3,575,911 | 4/1971 | Peterson | 260/29.6 |
| 3,975,350 | 8/1976 | Hudgin et al. | 260/30.4 N |
| 4,008,721 | 2/1977 | Burton | 128/418 |
| 4,082,705 | 4/1978 | Beede et al. | 260/4 R |
| 4,140,115 | 2/1979 | Schonfeld | 128/156 |
| 4,141,359 | 2/1979 | Jacobsen et al. | 128/172.1 |
| 4,170,612 | 10/1979 | Pastor et al. | 525/101 |
| 4,181,635 | 1/1980 | Takamatsu et al. | 260/5 |
| 4,226,915 | 10/1980 | Iijima et al. | 428/492 |

(List continued on next page.)

FOREIGN PATENT DOCUMENTS

| | | |
|---|---|---|
| 060431 | 9/1982 | European Pat. Off. |
| 60123416 | 12/1983 | Japan. |
| 1216268 | 12/1970 | United Kingdom. |
| 2115431 | 9/1983 | United Kingdom. |

OTHER PUBLICATIONS

Patent Abstracts of Japan, vol. 9, No. 278 (C-312)(2001)(Nov. 6, 1985) and JP, A,60123416 (Nitto Denki Kogyo K.K.) (Jul. 2, 1985) SEE Ohtsuka et al. above (w/translation).

Chemical Abstracts, vol. 86, No. 19 (May 9, 1977) J. F. MacDonald: "Pharmacology of dopamine receptors in the central nervous system of *Planorbis corneus,*" PCT, International Search Report, PCT/US90/00727, (Jul. 20, 1990) EPO, The Hague.

PCT, International Preliminary Examination Report, PCT/US90/00727, (Mar. 22, 1991) EPO, Munich.

*Primary Examiner*—Melvyn I. Marquis
*Assistant Examiner*—Randy Gulakowski
*Attorney, Agent, or Firm*—D. Byron Miller; Steven F. Stone; Edward L. Mandell

[57] ABSTRACT

A two phase adhesive matrix for use in an electrically powered iontophoretic delivery device is provided. The adhesive matrix comprises an adhesive hydrophobic polymer phase and about 15 to 60 wt % on a dry weight basis of a hydrophilic polymer phase distributed through the hydrophobic polymer phase. The hydrophilic phase forms upon hydration an interconnecting network of aqueous pathways for passage of the agent through the adhesive. The adhesive can be used to adhere an electrode assembly of an iontophoretic delivery device to a body surface such as skin or a mucosal membrane. Alternatively, the adhesive can be used to adhere together two or more elements of an iontophoretic delivery device.

18 Claims, 1 Drawing Sheet

U.S. PATENT DOCUMENTS

| | | | |
|---|---|---|---|
| 4,253,460 | 3/1981 | Chen et al. | 128/283 |
| 4,273,135 | 6/1981 | Larimore et al. | 128/640 |
| 4,274,420 | 6/1981 | Hymes | 128/641 |
| 4,356,819 | 11/1982 | Potaczek | 128/156 |
| 4,391,278 | 7/1983 | Cahalan et al. | 128/640 |
| 4,393,080 | 7/1983 | Pawelchak et al. | 428/355 |
| 4,393,150 | 7/1983 | Kresner | 523/111 |
| 4,456,741 | 6/1984 | Ames | 526/264 |
| 4,460,371 | 7/1984 | Abber | 604/897 |
| 4,474,570 | 10/1984 | Ariura et al. | 604/20 |
| 4,564,010 | 1/1986 | Coughlan et al. | 128/156 |
| 4,588,762 | 5/1986 | Mruk et al. | 524/49 |
| 4,655,767 | 4/1987 | Woodward et al. | 604/896 |
| 4,702,732 | 10/1987 | Powers et al. | 604/20 |
| 4,777,954 | 10/1988 | Keusch et al. | 128/802 |
| 4,780,411 | 10/1988 | Piejko et al. | 436/169 |
| 4,798,876 | 1/1989 | Gould et al. | 525/457 |
| 4,820,263 | 4/1989 | Spevak et al. | 128/802 |
| 4,830,776 | 5/1989 | Thompson | 128/802 |
| 4,860,754 | 8/1989 | Sharik et al. | 128/802 |
| 5,080,646 | 1/1992 | Theeuwes et al. | 128/802 |

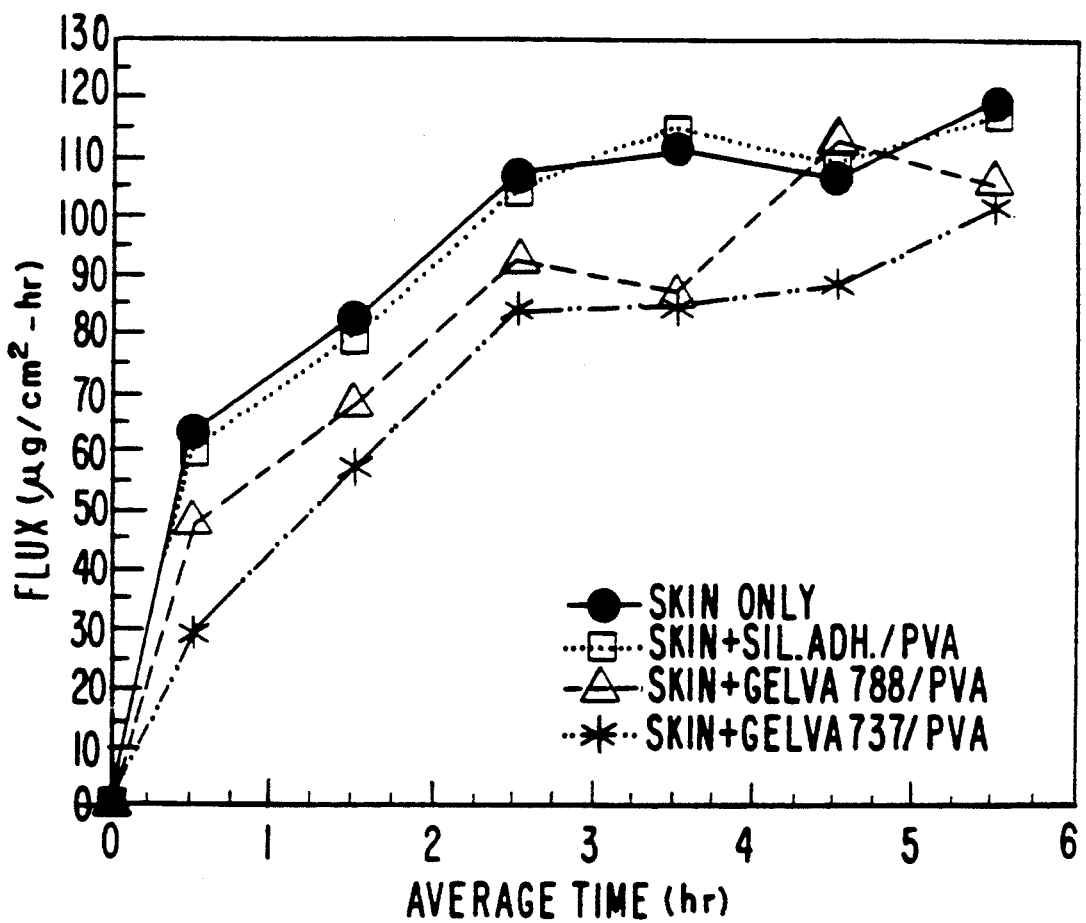

ELECTROTRANSPORT ADHESIVE

This case is a continuation of application Ser. No. 07/308,716, filed Feb. 9, 1989.

TECHNICAL FIELD

This invention relates to adhesive compositions. More particularly, this invention relates to adhesives for use as in-line contact adhesives for iontophoretic agent delivery devices. Still more particularly, but without limitation thereto, this invention relates to adhesives which permit the passage therethrough of therapeutic agents and electrolytes, especially water soluble and ionized agents and electrolytes.

BACKGROUND ART

Iontophoresis, according to Dorland3 s Illustrated Medical Dictionary, is defined to be "the introduction, by means of electric current, of ions of soluble salts into the tissues of the body for therapeutic purposes." Iontophoretic devices have been known since the early 1900's. British patent specification No. 410,009 (1934) describes an iontophoretic device which overcame one of the disadvantages of such early devices known to the art at that time, namely the requirement of a special low tension (low voltage) source of current which meant that the patient needed to be immobilized near such source. The device of that British specification was made by forming a galvanic cell from the electrodes and the material containing the medicament or drug to be delivered transdermally. The galvanic cell produced the current necessary for iontophoretically delivering the medicament. This ambulatory device thus permitted iontophoretic drug delivery with substantially less interference with the patient's daily activities.

More recently, a number of U.S. patents have issued in the iontophoresis field, indicating a renewed interest in this mode of drug delivery. For example, U.S. Pat. No. 3,991,755 issued to Vernon et al; U.S. Pat. No. 4,141,359 issued to Jacobsen et al; U.S. Pat. No. 4,398,545 issued to Wilson; and U.S. Pat. No. 4,250,878 issued to Jacobsen disclose examples of iontophoretic devices and some applications thereof. The iontophoresis process has been found to be useful in the transdermal administration of medicaments or drugs including lidocaine hydrochloride, hydrocortisone, fluoride, penicillin, dexamethasone sodium phosphate, insulin and many other drugs. Perhaps the most common use of iontophoresis is in diagnosing cystic fibrosis by delivering pilocarpine salts iontophoretically. The pilocarpine stimulates sweat production; the sweat is collected and analyzed for its chloride content to detect the presence of the disease.

In presently known iontophoretic devices, at least two electrodes are used. Both of these electrodes are disposed so as to be in intimate electrical contact with some portion of the skin of the body. One electrode, called the active or donor electrode, is the electrode from which the ionic substance, medicament, drug precursor or drug is delivered into the body by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be delivered into the body is positively charged (i.e., a cation), then the anode will be the active electrode and the cathode will serve to complete the circuit. If the ionic substance to be delivered is negatively charged (i.e., an anion), then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

It is also known that iontophoretic delivery devices can be used to deliver an uncharged drug or agent into the body. This is accomplished by a process called electroosmosis. Electroosmosis is the volume flow of a liquid (e.g., a liquid containing the uncharged drug or agent) through the skin induced by the presence of an electric field imposed across the skin.

Furthermore, existing iontophoresis devices generally require a reservoir or source of the beneficial agent (which is preferably an ionized or ionizable agent or a precursor of such agent) to be iontophoretically delivered or introduced into the body. Examples of such reservoirs or sources of ionized or ionizable agents include a pouch as described in the previously mentioned Jacobsen U.S. Pat. No. 4,250,878, or a pre-formed gel body as described in Webster U.S. Pat. No. 4,382,529 and Ariura et al. U.S. Pat. No. 4,474,570, which patents are incorporated herein by reference. Such drug reservoirs are electrically connected to the anode or the cathode of an iontophoresis device, or optionally to an electrolyte reservoir or an ion selective membrane, to provide a fixed or renewable source of one or more desired agents. See for example Parsi U.S. Pat. No. 4,731,049, incorporated herein by reference.

It is desirable to minimize the internal electrical resistance of an iontophoretic delivery device since this allows the device to be powered by a lower voltage, and therefore, less expensive, power source. One way of minimizing the internal electrical resistance of the device is to establish good electrical contact between the various components (e.g., the electrode, the drug reservoir, any electrolyte reservoir and any selectively permeable membrane) of the device as well as to establish good electrical contact between the device and the body surface (e.g., the skin or a mucosal membrane) through which the drug is to be delivered. Along with establishing an interface for ionic and/or water soluble species to diffuse, intimate contact between the delivery surface of the device and the body also ensures uniform electrical current distribution, thereby avoiding high localized current densities which could cause damage to body tissue.

Important criteria for adhesive compositions utilized as in-line contact adhesives for iontophoretic delivery devices in general, are: sufficient adhesion allowing prolonged adhesion to a body surface and allowing easy removal from the body surface without damaging the tissue, cohesion, bio- and chemical-compatibility, rapid drug transportability, and mechanical flexibility. When drugs are administered by electrotransport means rather than by passive diffusion, the adhesive should exhibit low resistance to drug transport and should contain minimal extraneous ions which could undesirably compete with the drug for delivery into the body.

The use of electrically-conductive adhesives in electrodes is known in the art. See U.S. Pat. No. 4,008,721, (vinyl acrylic copolymer which is activated by acetone or a low molecular weight alcohol); U.S. Pat. No. 4 391,278; (polymerized 2-acrylamido-2-methylpropane-sulfonic acid); U.S. Pat. No. 4,274,420; (karaya gum having an ionizable salt or a finely powdered metal dispersed therethrough); and U.S. Pat. No. 4,566,762 (cross-linked latex polymers containing an electrically conductive aqueous phase). While these adhesives are suitable for conducting current, they are not well suited for allowing agent or electrolyte (e.g., drug ions and/or electrolyte ions) to be transported therethrough. In addition, the solvent used in the adhesive may react adversely with the drug or hinder the delivery of drug to the body, or constituents incorporated in the adhesive may interfere with or compete with the agent or electrolyte for transport into the body.

Others have attempted to use self-adhering matrices comprised of a gel formed from a hydrophilic natural or synthetic material such as a natural resinous polysaccharide, plasticized with water and/or polyols. See U.S. Pat. Nos. 4,474,570 and 4,706,680.

This invention therefore provides an adhesive formulation which overcomes many of the disadvantages associated with state of the art adhesives and is particularly suited for use as an in-line contact adhesive used to (1) adhere an iontophoretic delivery device to a body surface such as skin or a mucosal membrane and/or (2) to adhere together two or more elements of an iontophoretic delivery device electrode assembly, through which elements drug and/or electrolyte ions must travel.

It is an object of this invention to provide an adhesive formulation suitable for use as an in-line contact adhesive for electrically assisted drug delivery systems.

It is a further object of this invention to provide an adhesive which has an acceptably low resistance to ionic transport when in a hydrated state.

It is a still further object of this invention to provide such an adhesive having uniform charge distribution properties.

DISCLOSURE OF THE INVENTION

These and other objects, features and advantages are met by an agent/electrolyte-conducting adhesive for use in an iontophoretic delivery device adapted to iontophoretically deliver an agent, preferably in the form of agent ions, through a body surface such as intact skin or a mucosal membrane. The adhesive is a two phase matrix comprised of an adhesive hydrophobic polymer phase and about 15 to 60 wt % on a dry weight basis of a hydrophilic polymer phase distributed through the hydrophobic polymer phase so as to form an interconnecting network of the hydrophilic polymer throughout the matrix. The interconnecting hydrophilic polymer network provides aqueous pathways for passage of the agent or electrolyte through the matrix.

Also provided is an electrically powered iontophoretic agent delivery device adapted to iontophoretically deliver an agent, such as a drug, through a body surface such as intact skin or a mucosal membrane. The delivery device includes a donor electrode assembly, a counter electrode assembly and a source of electrical power adapted to be electrically connected to the donor electrode assembly and the counter electrode assembly. The donor electrode assembly includes an agent reservoir containing the agent to be delivered. The agent reservoir is adapted to be placed in agent transmitting relation with a body surface. The donor electrode assembly also includes a donor electrode adapted to be electrically connected to the source of electrical power. The donor electrode is also in electrical contact with the agent reservoir.

According to one embodiment, the agent-conducting adhesive is disposed between the donor electrode assembly and the body surface in order to adhere the electrode assembly to the body surface. In an alternative embodiment, the adhesive is used to adhere the agent reservoir to the donor electrode and/or to another component in the donor electrode assembly such as an electrolyte reservoir or a membrane. In either case, the adhesive is a two phase matrix comprised of an adhesive hydrophobic polymer phase and about 15 to 60 wt % on a dry weight basis of a hydrophilic polymer phase distributed through the hydrophobic polymer phase so as to form an interconnecting network of the hydrophilic polymer throughout the matrix.

Preferably, the iontophoretic agent delivery device includes a counter electrode assembly having an electrolyte reservoir and a counter electrode in electrical contact with one another. The electrolyte reservoir in the counter electrode assembly is adapted to be placed in electrolyte transmitting relation with the body surface spaced apart from the donor electrode assembly. The electrolyte-conducting adhesive is disposed between the electrolyte reservoir and the body surface. The adhesive may also be used to adhere the electrolyte reservoir to the counter electrode and/or to another component in the counter electrode assembly such as a second reservoir or a membrane.

BRIEF DESCRIPTION OF THE DRAWING

The FIGURE is a graph presenting the electrically assisted flux of metoclopramide through several adhesive formulations of this invention, while the formulations are adhered to skin.

MOOES FOR CARRYING OUT THE INVENTION

As used herein, the terms "iontophoresis," "electrotransport" and "electrically assisted transport" are used interchangeably and are defined as the mechanism by which drugs are transported through a body surface under the influence of an electrical field. The term "body surface" as used herein, is defined as including without limitation, skin, body tissues, mucosal membranes, nails and blood vessel walls. As used herein, the expressions "agent" and "drug" are used interchangeably and are intended to have their broadest interpretation as any therapeutically active substance which is delivered to a living organism to produce a desired, usually beneficial effect.

This invention is an agent-conducting and electrolyte-conducting adhesive. The adhesive is a two phase matrix comprised of an adhesive hydrophobic polymer phase and a hydrophilic polymer phase which when hydrated provide an aqueous network for passage of agent/electrolyte through the adhesive matrix. The hydrophilic polymer phase is water sorbable and preferably non-ionic. The hydrophilic polymer phase can be either water soluble or water insoluble. The hydrophilic polymer phase functions as a hydroattractant material, forming aqueous pathways in the adhesive hydrophobic polymer matrix, through which the agent and electrolyte ions can pass through the adhesive.

The adhesive can be either in a dry or a hydrated state when applied to the body surface, depending upon the delivery profile desired or depending upon the stability of the other constituents, for example the drug or electrodes, when water is present. Utilizing the adhesive in a hydrated state may facilitate the onset of drug delivery as the pathways for drug/electrolyte passage will be immediately available. Hydrating the adhesive can be accomplished in several ways. The adhesive can be hydrated before packaging or it can be hydrated immediately prior to placement on the body surface. Alternately the aqueous source can be incorporated into the electrotransport drug delivery system with a barrier separating the source from the adhesive, said barrier being broken or removed immediately prior to use so as to hydrate the adhesive.

It may further be desirable to place a set amount of the agent to be delivered in the adhesive itself to provide a priming dose of agent when the system is placed on the body surface. Alternately, the adhesive itself may be the drug reservoir to form a self adhering drug reservoir. To function as a reservoir, the adhesive must contain agent in an amount sufficient to maintain therapeutic delivery for an extended period of time. The adhesive may also have other additives present such as are commonly known in the art. These include, plasticizers which may modify the tack and cohesive strength of the adhesive, fillers which may reduce the cost and improve handling, and antioxidants which improve the resistance of the adhesive to oxidative degradation.

Blending of the hydrophobic and hydrophilic polymer components is done mechanically, either in solution or by milling, extrusion or hot melt mixing, for example. The resulting adhesive films may then be prepared by solvent casting, extrusion or by melt processing, for example.

State of the art adhesives which are comprised of hydrophobic polymers, normally are only capable of absorbing less than 2% of their own weight in water. The presence of water and the resulting aqueous pathways is critical to the success of this invention and the addition of the hydrophilic polymer phase to the hydrophobic polymer creates an adhesive which is capable of absorbing water within the range of about 7 to 80% of the total adhesive weight.

The hydrophilic polymer phase can be present within the range of about 15 to 60 wt % on a dry weight basis, with the preferred range being about 30 to 40 wt % on a dry weight basis. The hydrophobic polymer phase comprises about 40 to 85 wt % on a dry weight basis, and preferably about 60 to 70 wt % on a dry weight basis, of the adhesive matrix. A suitable amount of hydrophilic polymer is that which provides an interconnecting network of the hydrophilic polymer throughout the matrix, generally at least about 15 wt % hydrophilic polymer. On the other hand, the amount of the hydrophilic polymer should not be so great that it significantly lowers the adhesive strength of the adhesive, generally no more than about 60 wt %. Keeping this criteria in mind, increasing the amount of hydrophilic polymer within this range will increase the current distribution but will also decrease the adhesive strength.

Preferably, the hydrophilic polymer is mixed with the hydrophobic polymer in the form of hydrophilic polymer particles. The average particle size can be up to about 180 μm. The particle size selected is preferably related to the thickness of the adhesive. For a 5 mil thick adhesive, the average particle size should be no larger than about 125 μm. For 2–3 mil thick adhesives, the preferred particle size is less than about 40 μm.

The hydrophobic polymer itself can have adequate adhesive properties or it may be rendered adhesive by the addition of tackifying resins.

Suitable hydrophobic polymers include, without limitation, acrylic or methacrylic resins such as polymers of esters of acrylic or methacrylic acid with alcohols such as n-butanol, n-pentanol, isopentanol, 2-methyl butanol, 1-methyl butanol, 1-methyl pentanol, 2-methyl pentanol, 3-methyl pentanol, 2-ethyl butanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, itaconic acid, ethylene vinylacetate copolymers, N-branched alkyl maleamic acids wherein the alkyl group had 10–24 carbon atoms, glycol diacrylates, or mixtures of these. Typical examples of commercially available acrylate adhesives suitable for use in this invention are the polyvinylacetate compounds sold by Monsanto Polymer Products Co. under the name of GELVA, such as GELVA 737 and GELVA 788, acrylate adhesives sold by the 3M Company such as 3M #9871 and 3M #9872, and sold by The Kendall Company under the name Kendall A200C-0. Also suitable are silicone adhesives which are prepared by the reaction of a linear polydimethylsiloxane fluid with a solvent-soluble, low molecular weight silicate resin. A typical example of a silicone adhesive suitable for use in this invention is a medical grade silicone pressure-sensitive adhesive commercially available under the trademark DOW CORNING ®355 Medical Grade Adhesive from Dow Corning Corporation. Plasticizers may also be added. A preferred plasticizer for silicone adhesives is silicone medical fluid.

Suitable hydrophobic polymers which can be rendered adhesive by the addition of tackifying resins include, without limitation, poly(styrene-butadiene) and poly(styrene-isoprene-styrene) block copolymers, ethylene vinyl acetate polymers such as those which are described in U.S. Pat. No. 4,144,317, plasticized or unplasticized polyvinylchoride, natural or synthetic rubbers, $C_2$–$C_4$ polyolefins such as polyethylene, polyisoprene, polyisobutylene and polybutadiene. Examples of suitable tackifying resins include, without limitation, fully hydrogenated aromatic hydrocarbon resins, hydrogenated esters and low molecular weight grades of polyisobutylene. Particularly suitable are tackifiers sold under the trademarks Staybelite Ester ® #5 and #10, Regal-Rez ® and Piccotac ®, by Hercules, Inc. of Wilmington, Del.

Suitable hydrophilic polymers include, without limitation, polyacrylamide (hereinafter "PAA"), Klucel ®, cross-linked dextran such as Sephadex (Pharmacia Fine Chemicals, AB, Uppsala, Sweden), polyvinylalcohol (hereinafter "PVA"), WaterLock (Grain Processing Corp., Muscatine, Iowa) which is a starch-graft-poly(-sodium acrylate-co-acrylamide) polymer, cellulosic derivatives such as hydroxypropylmethylcellulose (hereinafter "HPMC"), low-substituted hydroxypropylcellulose (hereinafter "LHPC") and cross-linked Nacarboxymethylcellulose such as Ac-Di-Sol (FMC Corp., Philadelphia, Pa.), hydrogels such as polyhydroxyethyl methacrylate (hereinafter "pHEMA") (National Patent Development Corp.), blends of polyoxyethylene or polyethylene glycols with polyacrylic acid such as Polyox ® blended with Carbopol ®, cross-linked polyvinyl pyrrolidone (hereinafter "PVP") (GAF Corporation), natural gums and chitosan. Also suitable are phospholipids such as L-α-phosphatidylcholine (Sigma Chemical Company).

The two phase adhesive matrix according to this invention has hydrophilic pathways in order to allow agent and/or electrolyte (e.g., agent or electrolyte ions) to pass through the adhesive under the influence of an electric field, i.e., the adhesive presents minimal mass transport resistance. The adhesive also has good hydration kinetics so that the time it takes to absorb water (e.g., from the body) and begin passing current, is acceptable. A suitable time to reach steady state moisture content is less than about 5 hours, preferably less than 1 hour, most preferably less than 10 minutes. Further, the adhesive layer provides for uniform current distribution so as to avoid highly localized current densities which could result in tissue damage.

The adhesive of the present invention exhibits excellent ionic conductivity so it is not rate limiting and does not require significant voltage during system operation, i.e., the adhesive presents minimal electrical resistance. State of the art adhesives have been shown to be essentially blocking to ionic transport in that ions are unable to pass through the adhesive. By incorporating the hydrophilic polymer phase, the adhesive of this invention has been shown to exhibit an area resistance of less than about 10 kohm-cm$^2$, preferably less than about 5 kohm-cm$^2$, most preferably less than about 1 kohm-cm$^2$ for a typical 3 mil thick sample, or most preferably less than about 0.33 kohm-cm$^2$ per mil thickness of adhesive.

Having thus generally described our invention, the following examples will illustrate how variations of the above described parameters provide adhesives suitable for use as in-line contact adhesives for electrotransport systems.

EXAMPLE I

Several acrylate-based adhesive formulations were tested in vitro to evaluate the electrically assisted and passive transport of the drug metoclopramide. Adhesive samples 5 mils in thickness were laminated onto flexible polyester cloth for support and mounted into cells designed for electrotransport permeation experiments. The sample side having exposed adhesive was positioned toward the anode. An aqueous donor solution containing 0.1 g/ml metoclopramide HCl was placed on the anode side of the cell. The receptor solution was Dulbecco's phosphate buffered saline at pH 7 and a total salt concentration of about 0.15M (hereinafter "DPBS"). Experiments were conducted at 32° C. for 5 hours. Metoclopramide transport across the adhesive/cloth laminate was measured, both with and without 0.1 mA/cm$^2$ of applied electrical current. The receptor solution was sampled and the cell voltage across the films was monitored every hour. The hydrophobic polymer used was Kendall A200C-0, an acrylate adhesive. The hydrophilic polymer was pHEMA, in the form of particles loaded in 20, 30, and 40 weight percent (wt %) amounts. The average particle size was within the range of 74–177 μm. Both electrically assisted and passive transport of metoclopramide through the Kendall A200C-0/pHEMA adhesives was high, exceeding 1 mg/cm$^2$-hr, thus establishing that the adhesives presented minimal mass transport resistance.

EXAMPLE II

Several adhesive films according to this invention were solvent cast and tested in vitro (32° C.) to measure the cell potential during electrically assisted transport of metoclopramide. The aqueous donor solution contained 0.1 g/ml metoclopramide and the receptor solution was DPBS. The cells had an anodic polarity and were run at a current of 0.1 mA/cm$^2$. The films tested were comprised of 70 wt % hydrophobic polymer and 30 wt % hydrophilic polymers. The hydrophobic polymers tested were silicone adhesive and the acrylate adhesives GELVA 788 and GELVA 737. The hydrophilic polymers tested was LHPC, in the form of particles having an average particle size of less than 63 μm. Control adhesive films comprised solely of hydrophobic polymer were also tested. The potentials across each cell and the equivalent resistances are presented in the following table:

TABLE I

| Adhesive | Potential (volts) | Area Resistance (kohm-cm$^2$) | Specific Resistance (kohm-cm$^2$/mil) | Thickness (mils) |
|---|---|---|---|---|
| Silicone Adhesive/LHPC | 0.084 | 0.84 | 0.28 | 3 |
| GELVA 788/LHPC | 0.024 | 0.24 | 0.10 | 2.5 |
| GELVA 737/LHPC | 0.016 | 0.16 | 0.05 | 3 |
| Silicone Adhesive | >30 | >200 | >100 | 2 |
| GELVA 788 | 4.6 | 46 | 18 | 2.5 |
| GELVA 737 | 3 | 30 | 20 | 1.5 |

As shown in Table I, the two phase adhesive matrices comprised of 30 wt % hydrophilic polymer exhibited specific resistances well within the most preferred range of less than 0.33 kohm-cm$^2$ per mil thickness of adhesive, and therefore have low voltage requirements during use. In comparison, the adhesive films having no hydrophilic additive exhibited area resistances at least 2 orders of magnitude higher than those of the present invention.

EXAMPLE III

Several adhesive films having an approximate thickness of 3 mils were made according to this invention, having a composition of 70 wt % hydrophobic polymer (silicone adhesive, GELVA 788 and GELVA 737) and 30 wt % hydrophilic polymer (PVA, particles having an average particle size of <63 μm). These adhesives were solvent cast, adhered to human cadaver skin and tested as in Example II. Two samples of each adhesive were run using eight skin samples from the same donor. The electrically assisted flux using 0.1 mA/cm$^2$ (averaged for the two samples) for metoclopramide versus time is plotted in the FIGURE and the voltages across each cell are presented in the following table:

TABLE II

| Adhesive | Cell Voltage (volts) | |
|---|---|---|
| | Sample 1 | Sample 2 |
| Skin only | 1.59 | 0.83 |
| Skin + Silicone Adhesive/PVA | 0.66 | 0.75 |
| Skin + GELVA 788/PVA | 0.75 | 0.81 |
| Skin + GELVA 737/PVA | 1.20 | 1.50 |

The data in the FIGURE establishes that the flux across skin does not change appreciably when the adhesive of this invention is added. This is desirable as the adhesive should not present a significant barrier to mass transport. The data in Table II also indicates that the voltage across the skin only has a fairly broad variability between different skin samples (0.83 to 1.59 volts). However, within this range the data shows that the cell voltage does not significantly increase when the adhesive of this invention is placed on the skin. Therefore, the adhesive itself appears to have a much lower electrical resistance than the resistance of the skin alone.

EXAMPLE IV

The acrylate-based adhesives of Example I were also tested as to their electrical resistance. The resistance of the Kendall A200C-0/pHEMA adhesives were on the order of 1 kohm-cm$^2$. The electrical resistance of the Kendall A200C-0 acrylate adhesive without any pHEMA added was approximately 15 kohm-cm$^2$.

EXAMPLE V

Several adhesive film compositions were evaluated for current distribution characteristics. The hydrophobic polymers used were silicone adhesive alone, silicone adhesive with silicone medical fluid and the acrylate adhesives GELVA 788 and GELVA 737. The hydrophilic polymers were either LHPC or PVA particles, having an average particle size of less than 63 μm. The adhesives were directly cast in thicknesses of approximately 3 mils onto copper foil and mounted as the anode in an electrochemical cell. The cathode was Ag-/AgCl and the electrolyte solution was 0.1M copper sulfate/0.5M sulfuric acid/0.01M sodium chloride solution. The test was run at room temperature for 6 hours at a current density of 0.5 mA/cm$^2$. As current flows, copper metal is oxidized underneath the adhesive film. At the conclusion of the experiment, the adhesive was dissolved from the copper foil and the surface of the foil inspected for uniformity of copper dissolution. The following data was obtained where hydration time was the time to reach 75% of the steady state voltage.

EXAMPLE VI

Electrochemical dissolution of a metal in intimate contact with a polymeric film occurs at the hydrated hydrophilic polymer pathways. Therefore, the electrical current distribution across an adhesive is revealed by observing the dissolution pattern created on a metal foil covered or coated by an adhesive. An 80 wt % Kendall A200C-0/20 wt % pHEMA particles (average particle size within the range of 74-177 μm) adhesive film was cast onto copper foil (0.0025 mm thick) to a dried film thickness of 5 mils. The copper/adhesive laminate was then mounted as the anode in an electrochemical cell. The cathode was Ag/AgCl and a 0.5M sulfuric acid/0.01M sodium chloride solution was used as the electrolyte solution. Triplicate samples of copper-/adhesive were evaluated for 1, 4, 8 and 24 hours using a current of 0.1 mA/cm$^2$. An uncoated copper foil was also included for each set of samples Following dissolution, the samples were rinsed with water, the adhesive layer was dissolved using methylene chloride, and the dissolution pattern on the copper surface was observed. Between 1 and 8 hours, no holes had formed on the coated sample, but the surface showed scattered minute dark spots, no larger than the diameter of a pin, which probably consisted of copper oxide. In contrast, the uncoated sample was uniformly discolored. After 24 hours, randomly dispersed holes (pinhole size or smaller) were observed on the coated sample. After 24 hours, discoloration of the uncoated sample was uniform, but darker than at 8 hours. Comparison of the dissolution patterns of the adhesive coated and uncoated foil samples indicated that the electrical current distribution across the adhesive was adequately distributed across the surface as evidenced by the random dispersion of pits and holes Increasing the loading of pHEMA and decreasing the particle size improves the current distribution since increased pHEMA loadings

TABLE III

| Weight Percent | | | | | | Hydration Time | Avg. Steady State Cell |
| --- | --- | --- | --- | --- | --- | --- | --- |
| Silicone Adhesive | Silicone Med. fluid | GELVA 788 | GELVA 737 | LHPC | PVA | (hours) | Voltage (volts) |
| 80 | | | | 20 | | <3.1 | 0.22 |
| 70 | | | | 30 | | <1 | 0.123 |
| | | 70 | | 30 | | <0.25 | 0.202 |
| | | | 70 | 30 | | <0.25 | 0.2 |
| | | 60 | | 40 | | <0.1 | 0.13 |
| | | | 60 | 40 | | <0.25 | 0.11 |
| 67.5 | 2.5 | | | 30 | | <1.6 | 0.18 |
| 57.5 | 2.5 | | | 40 | | <1 | 0.1 |
| 55 | 5 | | | 40 | | <1 | 0.11 |
| 80 | | | | | 20 | <0.5 | 0.31 |
| 70 | | | | | 30 | <0.25 | 0.15 |
| | | 70 | | | 30 | <0.25 | 0.12 |
| | | | 70 | | 30 | <0.5 | 0.48 |
| 67.5 | 2.5 | | | | 30 | <0.5 | 0.14 | while lower voltages are preferable, this is not always an indication of a better adhesive film since a low voltage (or low adhesive resistance) may be due to the presence of isolated defects in the adhesive, where all the current could pass through a small area rather than being uniformly distributed over the entire surface of the adhesive. The silicone adhesive formulations ehibited lower overall steady state voltages but showed spots of high current density. The acrylate adhesives showed a more uniform current distribution pattern and shorter hydration times, with the steady state voltages of GELVA 788 being somewhat greater than those of GELVA 737.

increase the density of hydrated hydrophilic polymer pathways per unit area.

EXAMPLE VII

Several acrylate-based adhesive formulations were tested as to tack or "stickiness". Kendall A200C-0 was loaded with 20, 30 and 40 wt % pHEMA particles (average particle size within the range of 74-177μ). All three films were tacky. Tack was highest for the film with 20 wt % pHEMA and lowest for the film with 40 wt % pHEMA. Additionally, silicone based adhesives containing various levels of pHEMA and acrylate adhesives (e.g., GELVA 788 and GELVA 737) containing various levels of pHEMA were compared All formulations tested exhibited sufficient tack and elasticity for use in an electrotransport transdermal system.

EXAMPLE VIII

Prolonged adhesion to the skin was evaluated using ½" diameter patches composed of 70 wt % Kendall A200C-0/30 wt % pHEMA particles (average particle size within the range of 74–177 μm) films laminated to flexible polyester cloth backing (non-occlusive) and to ethylene vinylacetate coated polyester film (occlusive). These patches were worn on the arm by several subjects After 7 hours, the patches were still adhering to the skin. No difference in wearability was observed regardless of which backing material was used.

EXAMPLE IX

Several adhesive formulations according to this invention were solvent cast as approximately 3 mil thick films having a disc area of 11.4 cm$^2$. The total water uptake was then evaluated by placing the formulations in a glass desiccator chamber, preheated to 32° C., containing a saturated solution of $Na_2HPO_4 \cdot 7H_2O$ which produced a 95% relative humidity atmosphere. Water uptake was measured by the total water absorbed (% dry basis). The adhesive compositions tested were comprised of 70 wt % hydrophobic polymer and 30 wt % hydrophilic polymer in the form of particles having an average particle size of <63μ. The hydrophilic polymers tested were LHPC (equilibrium moisture content=20.5% at 95% relative humidity), PVA (equilibrium moisture content=34.5% at 95% relative humidity) and PAA. The hydrophobic polymers tested were silicone adhesive, GELVA 788 and GELVA 737.

TABLE IV

| Hydrophilic Polymer | Hydrophobic Polymer | Time, hrs | Total Water Absorbed % of particle wt | % of adhesive wt |
|---|---|---|---|---|
| — | Sil. Adhesive | 8 | 0 | 0 |
| | GELVA 788 | 8 | 0 | 0 |
| | GELVA 737 | 8 | 0 | 0 |
| LHPC | Sil. Adhesive | 8.5 | 12.5 | 3.8 |
| | GELVA 788 | 8.5 | 23.0 | 6.9 |
| | GELVA 737 | 8.5 | 19.5 | 5.3 |
| PVA | Sil. Adhesive | 8.2 | 21.0 | 6.3 |
| | GELVA 788 | 8.2 | 20.5 | 6.2 |
| | GELVA 737 | 8.2 | 19.5 | 5.9 |
| PAA | Sil. Adhesive | 8.2 | 51 | 15.3 |
| | GELVA 788 | 8.2 | 60 | 18.0 |
| | GELVA 737 | 8.2 | 59 | 17.7 |

EXAMPLE X

A solid drug reservoir composed of 50 wt % hydroxypropylmethylcellulose and 50 wt % metoclopramide HCl was solvent cast from an aqueous solution to form a film. After drying, a 1" diameter disk of the film was laminated between a 1" disk of silver foil and a 1" disk of the adhesive being tested. One control system was made comprised of only the metoclopramide-containing film and silver foil. The control system had no adhesive layer.

The adhesives were made by solvent casting from a freon solution. Each adhesive contained 68 wt % hydrophobic polymer matrix (Dow Corning X7-2920 silicone adhesive), 2 wt % of a resinous tackifying agent (silicone medical fluid) and 30 wt % of hydrophilic polymer particles.

After lamination, the systems were hydrated in a 95% relative humidity environment for 2 hours and 15 minutes. Following hydration, a 1" disk of heat stripped human cadaver epidermis was placed with the stratum corneum side facing the exposed adhesive surface.

The three adhesive-containing systems and the adhesive-free control system were then mounted in an electrotransport permeation cell having a permeation area of 1.26 cm$^2$. DPBS was used as a receptor solution The silver foil was anodically polarized and the current was controlled at 100 μA/cm$^2$ using a Princeton Applied Research Potentiostat/Galvanostat Model 363. The transport of metoclopramide into the receptor compartment was determined hourly over a period of 5 hours by measuring the UV absorbance of the receptor solutions at 310 nanometers using a Hewlett Packard Spectrophotometer Model 8452A. Steady state flux was achieved by the 3rd hour and calculated by taking the average flux over hours 3, 4 and 5. The average steady state flux of metoclopramide is given in Table V. A comparison with the control system (which had no adhesive) demonstrates that the steady state flux of metoclopramide was only minimally impeded by the presence of the adhesive.

TABLE V

| Adhesive No. | Hydrophilic Polymer | Avg. Cell Voltage (volts) | Steady State Flux (μg/cm$^2$-hr) |
|---|---|---|---|
| Control | — | 0.5 | 148 |
| 1 | Starch-graft-poly (Na acrylate-co-acrylamide)[1] | 3.4 | 129 |
| 2 | Polyvinyl pyrrolidone[2] | 2.4 | 115 |
| 3 | Polyethylene oxide[3] | 5.5 | 120 |

[1]Water Lock A-180 sold by Grain Processing Corp. of Muscatine. IA
[2]PVP-xl sold by GAF Corp
[3]Polyox ® sold by Union Carbide Corp.

Having thus generally described our invention and described in detail certain preferred embodiments thereof, it will be readily apparent that various modifications to the invention may be made by workers skilled in the art without departing from the scope of this invention as defined by the following claims.

What is claimed is:

1. A two phase adhesive matrix for use in an electrically powered intophoretic agent delivery device adapted to iontophoretically deliver an agent through a body surface, the adhesive comprising an adhesive hydrophobic polymer phase and about 15 to 60 wt % on a dry weight basis of a hydrophilic polymer phase distributed through the hydrophobic polymer phase, the hydrophilic phase forming upon hydration an interconnecting network of the hydrophilic polymer throughout the matrix, the network providing aqueous pathways for passage of the agent through the matrix.

2. The adhesive of claim 1, wherein the matrix comprises about 30 to 40 wt % on a dry weight basis of the hydrophilic polymer.

3. The adhesive of claim 1, wherein the adhesive is capable of absorbing about 7 to 80 wt % water based on the total weight of the adhesive.

4. The adhesive of claim 1, wherein the hydrophilic polymer is selected from the group consisting of polyacrylamide, cross-linked dextran, polyvinylalcohol, starch-graft-poly(sodium acrylate-co-acrylamide) polymers, hydroxypropylmethylcellulose, low-substituted hydroxypropylcellulose. cross-linked Na-carboxymethylcellulose, polyhydroxyethyl methacrylate, blends of polyoxyethylene and polyethylene glycols with polyacrylic acid, polyethylene oxides and cross-linked polyvinyl pyrrolidone.

5. The adhesive of claim 1, wherein the hydrophilic polymer is in the form of particles having a particle size of up to about 180 $\mu$m.

6. The adhesive of claim 5, wherein the hydrophilic particles have a particle size of up to about 35 $\mu$m.

7. The adhesive of claim 1, the adhesive exhibiting a specific resistance of less than about 0.33 kohm-cm$^2$ per mil thickness of adhesive.

8. The adhesive of claim 1, wherein the hydrophobic polymer is selected from the group consisting of acrylate adhesives and silicone adhesives.

9. The adhesive of claim 1, wherein the hydrophobic polymer phase is rendered adhesive by adding thereto a tackifying resin.

10. The adhesive of claim 9, wherein the hydrophobic polymer is selected from the group consisting of poly(styrene-isoprene-styrene) block copolymers, ethylene vinyl acetate polymers, plasticized and unplasticized polyvinylchloride, natural and synthetic rubber, $C_2$–$C_4$ polyolefins, polyethylene, polyisoprene, polyisobutylene and polybutadiene.

11. The adhesive of claim 9, wherein the tackifying resin is selected from the group consisting of fully hydrogenated aromatic hydrocarbon resins, hydrogenated esters and low molecular weight grades of polyisobutylene.

12. The adhesive of claim 1, wherein the adhesive matrix also contains at least a portion of the agent to be delivered.

13. The adhesive of claim 1, wherein the agent comprises a drug.

14. The adhesive of claim 13, wherein the drug comprises a water soluble drug salt.

15. The adhesive of claim 1, wherein the agent comprises an electrolyte.

16. The adhesive of claim 15, wherein the electrolyte comprises a water soluble electrolyte salt.

17. The adhesive of claim 1, wherein the hydrophilic polymer is a hydrogel.

18. The adhesive of claim 1, wherein the hydrophilic polymer is a cellulosic derivative.

* * * * *